(12) United States Patent
Koyama et al.

(10) Patent No.: US 10,376,606 B2
(45) Date of Patent: Aug. 13, 2019

(54) STERILIZING SHEET DEVICE

(71) Applicants: CREATIVE TECHNOLOGY CORPORATION, Kawasaki-shi, Kanagawa (JP); MATSUDA DESIGN LTD, Tokyo (JP)

(72) Inventors: Satomi Koyama, Kawasaki (JP); Yoshiaki Tatsumi, Kawasaki (JP); Li Luo, Kawasaki (JP); Kazuki Tsuboi, Kawasaki (JP); Mutsumi Kusano, Kawasaki (JP); Takeshi Matsuda, Tokyo (JP); Shujiro Hayashi, Tokyo (JP)

(73) Assignees: CREATIVE TECHNOLOGY CORPORATION, Kawasaki-Shi, Kanagawa (JP); MATSUDA DESIGN LTD, Tokyo (JP)

( * ) Notice: Subject to any disclaimer, the term of this patent is extended or adjusted under 35 U.S.C. 154(b) by 36 days.

(21) Appl. No.: 15/568,197

(22) PCT Filed: May 13, 2016

(86) PCT No.: PCT/JP2016/064387
§ 371 (c)(1),
(2) Date: Oct. 20, 2017

(87) PCT Pub. No.: WO2016/190139
PCT Pub. Date: Dec. 1, 2016

(65) Prior Publication Data
US 2018/0147308 A1 May 31, 2018

(30) Foreign Application Priority Data

May 27, 2015 (JP) .................................. 2015-107402

(51) Int. Cl.
*A61L 2/20* (2006.01)
*C01B 13/11* (2006.01)
(Continued)

(52) U.S. Cl.
CPC .............. *A61L 2/202* (2013.01); *A01N 59/00* (2013.01); *A61L 2/10* (2013.01); *C01B 13/11* (2013.01);
(Continued)

(58) Field of Classification Search
CPC ... A61L 2/202; A61L 2/10; A61L 2/26; A61L 2202/11; A61L 2202/16; A61L 2202/20; A61L 2202/26; A01N 59/00; C01B 13/11
See application file for complete search history.

(56) References Cited

U.S. PATENT DOCUMENTS 3,056,005 A * 9/1962 Larson ................... H01H 3/141
200/86 R
2004/0084759 A1* 5/2004 Miyagawa .......... H01L 23/5387
257/678

(Continued)

FOREIGN PATENT DOCUMENTS

JP    H07-309605 A    11/1995
JP    2000-219503 A    8/2000
(Continued)

OTHER PUBLICATIONS

PCT, "International Search Report for International Application No. PCT/JP2016/064387" dated Aug. 2, 2016.
(Continued)

*Primary Examiner* — Regina M Yoo
(74) *Attorney, Agent, or Firm* — Manabu Kanesaka

(57) ABSTRACT

A sterilizing sheet is excellent in terms of saving space when a sterilizing operation is being performed, and sterilizing objects of various sizes. This sterilizing sheet is provided
(Continued)

with a flexible sheet body, a sheet accommodating body and a handle. The sheet body is formed from a dielectric and a pair of electrodes accommodated inside the dielectric. The sheet accommodating body is a cylindrical body in which the sheet body is accommodated to be capable of being pulled out and rewound, and is provided with a case, a rotating body and a rewinding mechanism. The rewinding mechanism is a mechanism for automatically rewinding the sheet body, when pulled out from the sheet accommodating body, back into the sheet accommodating body. The handle is attached to a distal end portion of the sheet body, and includes, inside the handle, a battery, a switch mechanism, a booster circuit and a monitoring circuit.

8 Claims, 10 Drawing Sheets

(51) Int. Cl.
    *A61L 2/10*         (2006.01)
    *A01N 59/00*      (2006.01)
    *A61L 2/26*         (2006.01)

(52) U.S. Cl.
    CPC .............. *A61L 2/26* (2013.01); *A61L 2202/11* (2013.01); *A61L 2202/16* (2013.01); *A61L 2202/20* (2013.01); *A61L 2202/26* (2013.01)

(56) References Cited

U.S. PATENT DOCUMENTS

| | | | |
|---|---|---|---|
| 2012/0213664 A1 | 8/2012 | Diver et al. | |
| 2012/0259156 A1* | 10/2012 | Freeman | A61B 5/11 600/14 |
| 2013/0231046 A1* | 9/2013 | Pope | G06K 9/00013 455/41.1 |
| 2015/0371829 A1 | 12/2015 | Koyama et al. | |
| 2016/0154170 A1* | 6/2016 | Thompson | G02F 1/133603 362/609 |

FOREIGN PATENT DOCUMENTS

| | | |
|---|---|---|
| JP | 2004-313691 A | 11/2004 |
| JP | 2005-152035 A | 6/2005 |
| JP | 2010-220984 A | 10/2010 |
| JP | 2011-167463 A | 9/2011 |
| JP | 2013-510398 A | 3/2013 |
| WO | 2014/119349 A1 | 8/2014 |

OTHER PUBLICATIONS

Europe Patent Office, "Search Report for European Patent Application No. 16799847.5," dated Dec. 19, 2018.

* cited by examiner

STERILIZING SHEET DEVICE

RELATED APPLICATIONS

The present application is National Phase of International Application No. PCT/JP2016/064387 filed May 13, 2016, and claims priority from Japanese Application No. 2015-107402, filed May 27, 2015, the disclosure of which is hereby incorporated by reference herein in its entirety.

TECHNICAL FIELD

The present invention relates to a sterilizing sheet device for sterilizing sterilization target objects such as electronic devices.

BACKGROUND ART

In general, when cleaning dust off an electronic device such as a personal computer's keyboard, such a dedicated cleaning tool and/or an air blower as described in Patent Literature 1 are used, but these tools cannot remove bacteria attached to the electronic device.

Hence, when removing bacteria from the electronic device, cleaner and/or disinfectant must be used to clean them off. However, if the electronic device is, for example, a keyboard, after cleaning it off with cleaner, it must be wiped again, and it becomes necessary to perform these operations for many key buttons, which requires a great deal of time and effort. Also, when disinfectant is used, not only does it require time and effort for wiping with the disinfectant itself, but there is also a concern that the disinfectant may cause a rash or the like.

There has been proposed a disinfection apparatus described in Patent Literature 2, for example, as a technique capable of skipping such time-consuming operations.

The disinfection apparatus has a structure with which the box-like apparatus itself is put over a personal computer's keyboard or the like and then a disinfection lamp such as an ultraviolet lamp is turned on to irradiate the keyboard with disinfection light such as ultraviolet light for a certain period of time and thereby to allow killing bacteria attached to the keyboard.

CITATION LIST

Patent Literature

PLT1: Japanese Application Laid-Open No. 2004-313691
PLT2: Japanese Application Laid-Open No. 2010-220984

SUMMARY OF THE INVENTION

Technical Problem

However, the above-described conventional technique suffers from the following problems.

That is, since the above-described disinfection apparatus has a structure formed in a box shape and put over an electronic device such as a keyboard, the apparatus itself is likely to have a large size. It is therefore difficult to use the apparatus on a narrow desk.

Since the size of the box as the apparatus itself is also fixed, the apparatus cannot accommodate electronic devices of various sizes. Accordingly, in the case of sterilizing electronic devices of various sizes, it is necessary to create or buy apparatuses capable of accommodating these sizes.

Further, the apparatus cannot be disassembled or folded to reduce its size. A large space is therefore required to store the apparatus when not in use.

In addition, only the surface of the key buttons of a keyboard or the like is irradiated with disinfection light from the ultraviolet lamp. It is therefore difficult to sterilize the side surfaces of the key buttons and narrow gap portions at the back of the key buttons.

Sterilization target objects other than electronic devices also suffer from these problems.

The present invention has been made to solve the above-described problems, and an object thereof is to provide a sterilizing sheet which is excellent in terms of saving space when a sterilizing operation is performed, in terms of being capable of sterilizing sterilization target objects of various sizes, and in terms of being capable of being stored when not in use, and which can moreover sterilize sterilization target objects thoroughly.

Solution to the Problems

In order to solve the above-described problems, the invention of claim 1 is directed to a sterilizing sheet including: a flexible sheet body formed by a sheet-like dielectric and a pair of electrodes, at least one of the electrodes accommodated within the dielectric; a sheet accommodating body in which the sheet body is accommodated in a manner capable of being pulled out and rewound; and a handle attached to the leading end of the sheet body and in which a power source is accommodated capable of supplying a voltage necessary to generate ozone to the pair of electrodes.

With the arrangement above, the handle can be gripped in use to pull the sheet body out of the sheet accommodating body. By making the amount of pull-out of the sheet body match the size of a sterilization target object such as a keyboard, the flexible sheet body can be overlaid directly in accordance with the shape of the sterilization target object. It is therefore possible to sterilize the sterilization target object even on a narrow desk. That is, space saving can be achieved during the sterilizing operation.

Further, since the handle can be gripped to pull the sheet body out of the sheet accommodating body or rewind the sheet body back into the sheet accommodating body and thereby to adjust the length of the sheet body, the sterilizing sheet can by itself be used to sterilize not only the keyboard but also sterilization target objects of various sizes such as a mouse and a smartphone. That is, the sterilizing sheet according to the present invention has size compatibility that the sheet can by itself sterilize sterilization target objects of various sizes without creating or buying apparatuses capable of accommodating these sizes.

In this state, when the power source is turned on, ozone is generated from the sheet body to sterilize the sterilization target object. Upon this, the ozone, which is gaseous, warps around not only the surface of the keyboard but also the side surfaces of the key buttons and narrow gap portions at the back of the key buttons to moreover sterilize the sterilization target object thoroughly.

After completion of the sterilization, the power source can be turned off to stop the generation of ozone from the sheet body. The sheet body can then be rewound back into the sheet accommodating body to be entirely accommodated within the sheet accommodating body. In this state of accommodation of the sheet body, the sterilizing sheet has a compact form in which the sheet accommodating body and the handle are aligned. This causes no large space to be required for storing the sterilizing sheet. That is, the sterilizing sheet according to the present invention takes up little space for storage, exhibiting high storability when not in use.

The invention of claim 2 is directed to the sterilizing sheet according claim 1, in which at least the dielectric of the sheet body is formed of polymeric resin.

With the arrangement above, the sheet body, in which at least the dielectric is formed of polymeric resin, can generate ozone.

While ceramic is commonly used as a material of ozone generators, using such a sheet in which at least the dielectric is formed of polymeric resin as in the present invention as an ozone generator allows the thickness and weight of the sterilizing sheet to be reduced and the area of the ozone generation part to be increased.

The invention of claim 3 is directed to the sterilizing sheet according to claim 1 or 2, in which the pair of electrodes are each formed in a comb shape and the comb teeth of the pair of electrodes are engaged with each other at a regular interval.

With the arrangement above, a discharge phenomenon occurs between the pair of electrodes, in which the comb teeth are engaged with each other at a regular interval, whereby ozone is generated.

The invention of claim 4 is directed to the sterilizing sheet according to any one of claims 1 to 3, in which a rewinding mechanism is provided to automatically rewind the sheet body, when pulled out of the sheet accommodating body, back into the sheet accommodating body.

With the arrangement above, after the sheet body is pulled out of the sheet accommodating body, the rewinding mechanism can automatically rewind the pulled-out sheet body back into the sheet accommodating body.

The invention of claim 5 is directed to the sterilizing sheet according to any one of claims 1 to 4, in which the power source is a battery accommodated in the sheet accommodating body or the handle.

With the arrangement above, no cable from an external power source is required, and accordingly the size can be reduced and the portability can be increased.

The invention of claim 6 is directed to the sterilizing sheet according to claim 5, in which a switch mechanism is provided to turn on the power source when the sheet body is pulled out of the sheet accommodating body and turn off the power source when the sheet body is accommodated in the sheet accommodating body.

With the arrangement above, the switch mechanism turns on the power source when the sheet body is pulled out of the sheet accommodating body and turns off the power source when the sheet body is accommodated in the sheet accommodating body.

The invention of claim 7 is directed to the sterilizing sheet according to claim 5 or 6, in which a monitoring circuit for displaying some or all of the on or off state of the power source, the remaining battery power, and the operating time is provided on the sheet accommodating body or the handle.

With the arrangement above, the monitoring circuit can easily visualize the current state of the power source, the remaining battery power, and the operating time.

The invention of claim 8 is directed to the sterilizing sheet according to any one of claims 1, 2, 4 to 7, in which one of the pair of electrodes is accommodated within the dielectric and the other electrode with a number of holes or in a comb shape is disposed on the surface of the dielectric in a manner opposed to the one electrode.

Effects of the Invention

As described in detail hereinbefore, the sterilizing sheet according to the present invention can perform a sterilizing operation even on a narrow desk, exhibiting an effect of space saving during the sterilizing operation.

In addition, the sterilizing sheet according to the present invention can by itself sterilize sterilization target objects of various sizes, having high size compatibility.

The sterilizing sheet according to the present invention also exhibits an effect that not only the surface but every part of sterilization target objects can be sterilized.

Further, the sterilizing sheet according to the present invention takes up little space for storage, exhibiting high storability when not in use.

In particular, the invention of claim 2, in which the sheet in which at least the dielectric is formed of polymeric resin is used as an ozone generator, exhibits an effect that the thickness and weight of the sterilizing sheet can be reduced and the area of the ozone generation part can be increased.

Moreover, the invention of claim 5 exhibits an effect that the size can be reduced and the portability can be increased.

BRIEF DESCRIPTION OF THE DRAWINGS

FIG. 10 is a perspective view showing an example in which the sterilizing sheet is used to sterilize, for example, a desktop personal computer's keyboard and the like.

DESCRIPTION OF THE EMBODIMENTS

The best mode of the present invention will hereinafter be described with reference to the accompanying drawings.

First Embodiment

Figure 1:
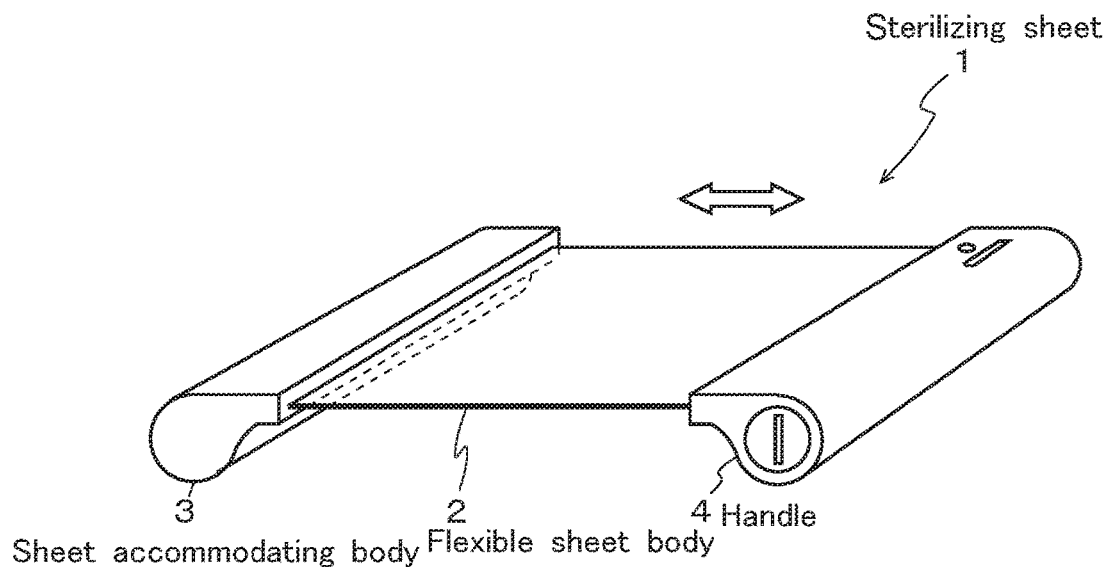
FIG. 1 is a perspective view showing a pulled-out state of a sterilizing sheet according to a first embodiment of the present invention.
Figure 2:
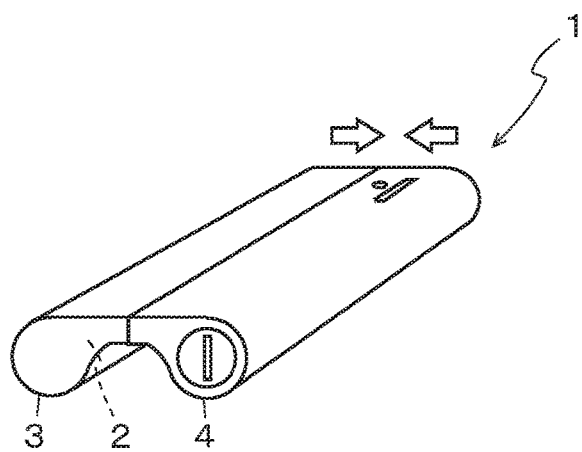
FIG. 2 is a perspective view showing an accommodated state of the sterilizing sheet.

FIG. 1 is a perspective view showing a pulled-out state of a sterilizing sheet according to a first embodiment of the present invention, and FIG. 2 is a perspective view showing an accommodated state of the sterilizing sheet.

As shown in FIG. 1, the sterilizing sheet 1 according to this embodiment includes a sheet body 2, a sheet accommodating body 3, and a handle 4.

The sheet body 2 is a flexible band body that generates ozone.

Figure 3:
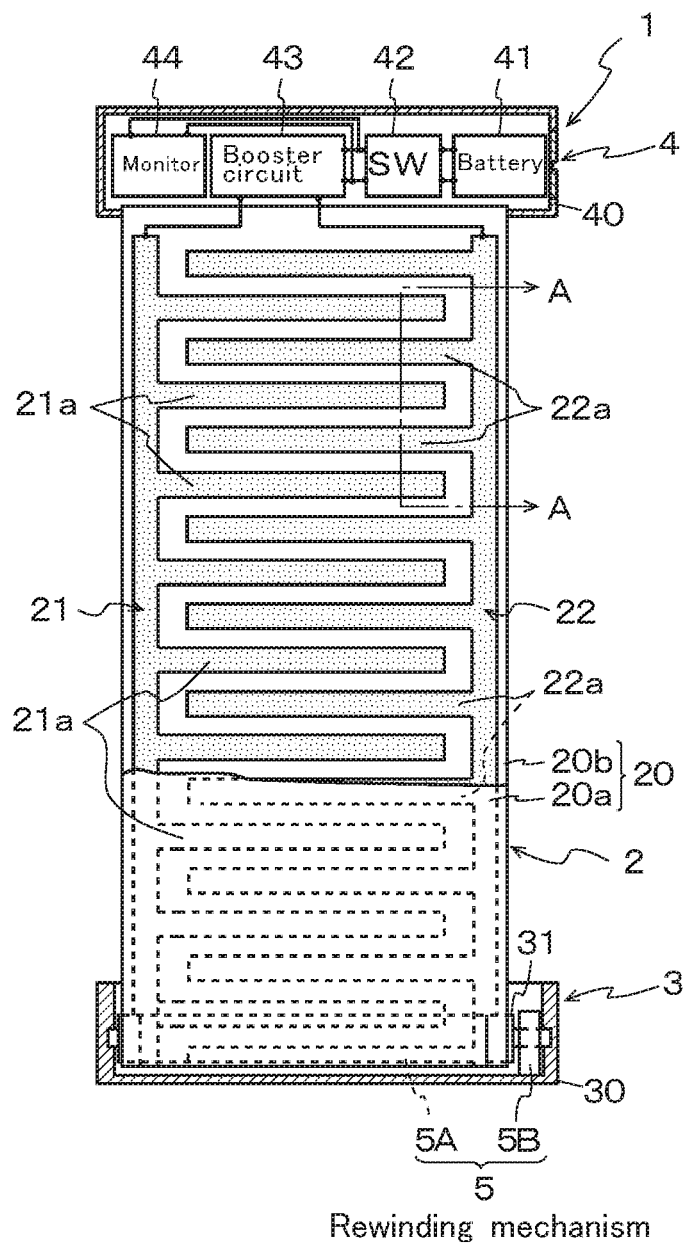
FIG. 3 is a cutaway schematic plan view of the sterilizing sheet.
Figure 4:
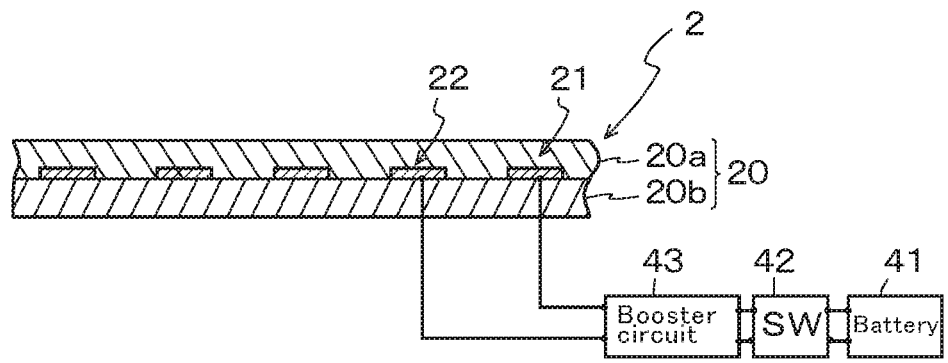
FIG. 4 is a cross-sectional view indicated by the arrows A-A in FIG. 3.

FIG. 3 is a cutaway schematic plan view of the sterilizing sheet, and FIG. 4 is a cross-sectional view indicated by the arrows A-A in FIG. 3.

As shown in FIG. 3, the sheet body 2 is formed by a sheet-like dielectric 20 and a pair of electrodes 21, 22 accommodated within the dielectric 20.

Specifically, as shown in FIG. 4, the dielectric 20 is formed of two dielectric layers 20a, 20b, in which the electrodes 21, 22 are formed on the lower dielectric layer 20b and the upper dielectric layer 20a is laminated on the dielectric layer 20b in a manner covering the electrodes 21, 22.

The thus arranged sheet body 2 is entirely formed of polymeric resin. In this embodiment, not only are the dielectric layers 20a, 20b respectively formed of polyimide resin, but the electrodes 21, 22 are also formed of conductive polymer, an example of polymeric resin. The sheet body 2 thus entirely formed of polymeric resin has increased flexibility as well as reduced thickness and weight of the sheet body 2, and allows the area of the ozone generation part sheet of the body 2 to be increased.

Further, as shown in FIG. 3, the pair of electrodes 21, 22 are each formed in a comb shape and the comb teeth 21a, 22a are engaged with each other at a regular interval.

The sheet accommodating body 3 is a cylindrical body in which the thus arranged sheet body 2 is accommodated in a manner capable of being pulled out and rewound.

Specifically, the sheet accommodating body 3 has a cylindrical case 30 and a rotating body 31 fitted rotatably within the case 30. The sheet body 2 is wound around the rotating body 31 with one end portion thereof being fastened to the rotating body 31. With this arrangement, when the one end portion of the sheet body 2 is pulled out of the case 30 (upward in FIG. 3), the rotating body 31 rotates, whereby the sheet body 2 can be pulled out of the case 30. When the rotating body 31 then rotates reversely, the sheet body 2 is rewound around the rotating body 31, whereby the entire sheet body 2 can be wound around the rotating body 31.

A rewinding mechanism 5 is assembled in the thus arranged sheet accommodating body 3.

The rewinding mechanism 5 is a mechanism for automatically rewinding the sheet body 2, when pulled out of the sheet accommodating body 3, back into the sheet accommodating body 3 and, in this embodiment, employs a technique similar to that described in Japanese Application Laid-Open No. 1996-296381.

Figure 5:
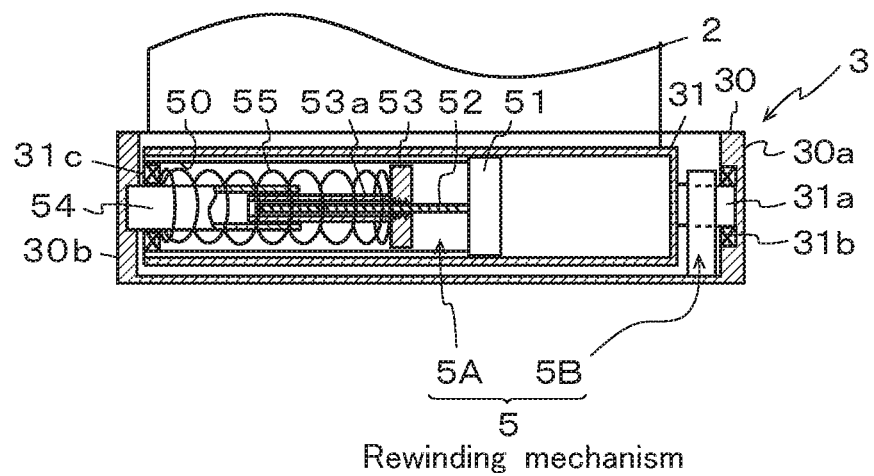
FIG. 5 is a schematic cross-sectional view of a rewinding mechanism.

FIG. 5 is a schematic cross-sectional view of the rewinding mechanism 5.

As shown in FIG. 5, the rewinding mechanism 5 consists of an elastic force accumulating part 5A and a stopper part 5B.

The elastic force accumulating part 5A is a part arranged to accumulate an elastic force for pulling back the sheet body 2 when pulled out.

Specifically, a right-hand shaft 31a of the cylindrical rotating body 31 with the sheet body 2 wound therearound is supported rotatably on the right wall 30a of the case 30 via a bearing 31b, and a cylindrical body 50 of the elastic force accumulating part 5A is fixed on the inner surface of the rotating body 31. Moreover, a planetary gear train 51 is fastened to a right end portion of the cylindrical body 50, and a spiral rod 52 is linked to a sun gear (not shown) of the planetary gear train 51. Further, a moving body 53 is threadably mounted on the spiral rod 52. The moving body 53 has a rectangular cylindrical body 53a protruding leftward in FIG. 5.

With the arrangement above, when the rotating body 31 rotates, the cylindrical body 50 of the elastic force accumulating part 5A rotates together with the rotating body 31 and also an internally toothed gear (not shown) of the planetary gear train 51 rotates. The rotation of the internally toothed gear is then transferred to the sun gear via multiple planetary gears not shown, whereby the spiral rod 52 rotates at a desired speed corresponding to the gear ratio.

On the other hand, a rectangular cylindrical body 54 protruding rightward is fastened to the left wall 30b of the case 30 and fitted to the rectangular cylindrical body 53a of the moving body 53.

A left end portion of the cylindrical body 50 is supported rotatably on the thus arranged rectangular cylindrical body 54 via a bearing 31c. Moreover, a coil spring 55 is fitted within the cylindrical body 50 and outside of the rectangular cylindrical body 54.

That is, the rectangular cylindrical body 54 is structured not to rotate even when the rotating body 31 and/or the cylindrical body 50 may rotate. With this arrangement, when the spiral rod 52 rotates, the moving body 53 attempts to rotate but cannot rotate because the rectangular cylindrical body 53a is fitted to the rectangular cylindrical body 54 in a fixed state. This causes the moving body 53 to move leftward and rightward on the spiral rod 52 depending on the direction of rotation of the spiral rod 52. As a result, when the moving body 53 moves leftward, the coil spring 55 is compressed so that an elastic force is accumulated. In reverse, when the moving body 53 moves rightward, the coil spring 55 is restored so that the elastic force accumulated in the coil spring 55 is released.

On the other hand, the stopper part 5B is formed by a conventionally well-known latch mechanism and has a function of allowing the rotating body 31 to rotate in the direction in which the sheet body 2 is pulled out and inhibiting the rotating body 31 from rotating in the direction in which the sheet body 2 is rewound. The stopper part 5B further has a function of releasing the rotation inhibited state of the rotating body 31 when the rotating body 31 is rotated slightly from the rotation inhibited state in the rotation allowance direction.

As shown in FIG. 3, the handle 4 is attached to the leading end portion of the sheet body 2 (upper end portion in FIG. 3), within which a battery 41 is accommodated to supply a voltage necessary to generate ozone to the electrodes 21, 22 of the sheet body 2.

Specifically, the handle 4 is formed in a cylindrical case 40 within which the battery 41 serving as a power source, a switch mechanism 42, a boosting circuit 43, and a monitoring circuit 44 are included.

The battery 41 is, for example, a dry cell with a direct-current voltage of 6 V and connected electrically to the boosting circuit 43 and the monitoring circuit 44 via the switch mechanism 42.

The boosting circuit 43 is a circuit for boosting the direct-current voltage of 6 V input from the battery 41 to an alternate-current voltage or a pulsed voltage of, for example, 2 kV to 10 kV and supplying the voltage to the electrodes 21, 22 of the sheet body 2.

The switch mechanism 42 is a mechanism for turning on the power source to the electrodes 21, 22 when the sheet body 2 is pulled out of the sheet accommodating body 3 and turning off the power source when the sheet body 2 is accommodated in the sheet accommodating body 3.

Figure 6:
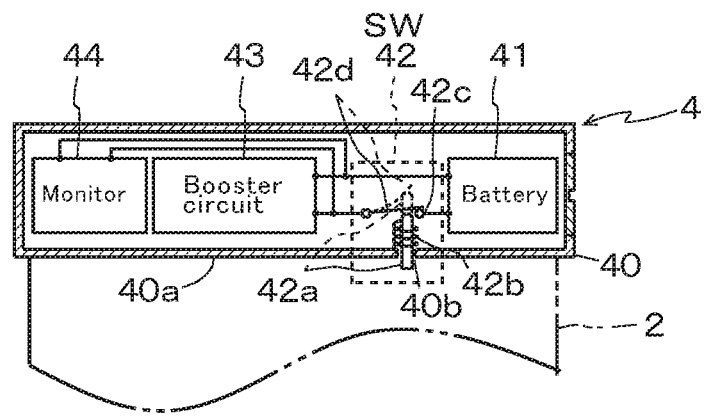
FIG. 6 is a schematic cross-sectional view showing the configuration of a switch mechanism.

FIG. 6 is a schematic cross-sectional view showing the configuration of the switch mechanism 42.

As shown in FIG. 6, the switch mechanism 42 includes a pin body 42a, a spring 42b, a fixed terminal 42c, and a movable terminal 42d.

The leading end of the pin body 42a is inserted in a hole 40b provided in the front wall 40a of the case 40. The spring 42b is then interposed between the pin body 42a and the case 40 to urge the pin body 42a to protrude outward from the front wall 40a.

On the other hand, the fixed terminal 42c is connected electrically to one of the output terminals of the battery 41, and the movable terminal 42d is connected electrically to one of the input terminals of the boosting circuit 43 and one of the input terminals of the monitoring circuit 44. The movable terminal 42d is a plate-spring-like metal body and, when not subject to an external force, in pressurized contact with the fixed terminal 42c from the rear (top in FIG. 6) toward the front (bottom in FIG. 6) of the case 40. Accordingly, the movable terminal 42d, when not subject to a pressing force from the pin body 42a, is in contact with the fixed terminal 42c. However, when the pin body 42a moves rearward to press the movable terminal 42d rearward as indicated by the broken line, the contact state between the movable terminal 42d and the fixed terminal 42c is released.

The monitoring circuit 44 is a circuit for displaying some or all of the on or off state of the power source, the remaining battery power, and the operating time.

Figure 7:
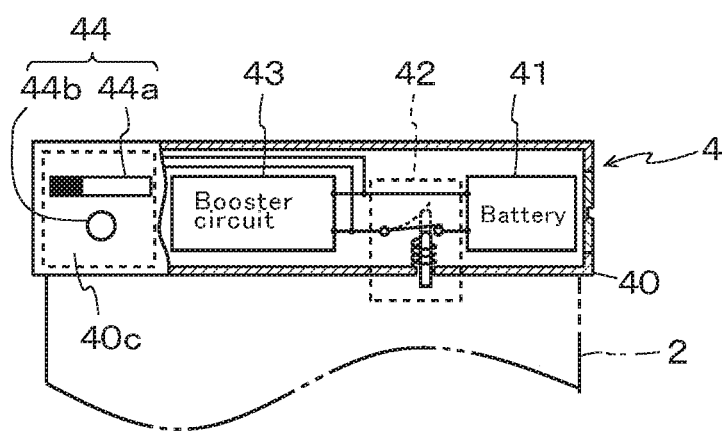
FIG. 7 is a schematic cross-sectional view of a remaining battery power meter and a power lamp of a monitoring circuit.

FIG. 7 is a schematic cross-sectional view of a remaining battery power meter and a power lamp of the monitoring circuit 44.

As shown in FIG. 7, the monitoring circuit 44 consists of the remaining battery power meter 44a and the power lamp 44b connected electrically to the battery 41 via the switch mechanism 42, and the remaining battery power meter 44a and the power lamp 44b are mounted on the upper wall 40c of the case 40. With this arrangement, when the switch mechanism 42 is closed and the battery 41 goes on, the power lamp 44b is turned on and the remaining battery power meter 44a displays the current remaining power of the battery 41.

Next will be described operations and effects of the sterilizing sheet 1 according to this embodiment.

Figure 8A:
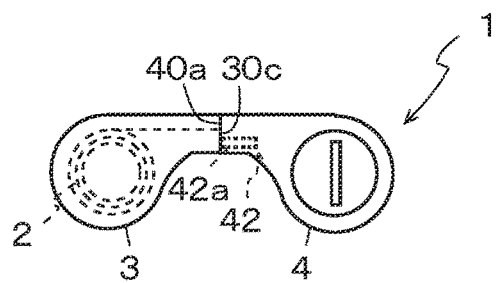
FIGS. 8(*a*) and 8(*b*) are side views showing examples of how the sterilizing sheets are used, where FIG. 8 (*a*) shows a state where a sheet body is accommodated in a sheet accommodating body and FIG. 8 (*b*) shows a state where the sheet body is pulled out of the sheet accommodating body.
Figure 8B:
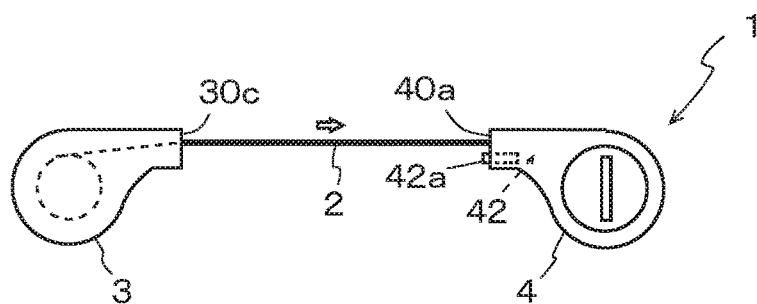

FIG. 8 is a side view showing an example of how the sterilizing sheet 1 is used, where FIG. 8 (a) shows a state where the sheet body 2 is accommodated in the sheet accommodating body 3 and FIG. 8 (b) shows a state where the sheet body 2 is pulled out of the sheet accommodating body 3.

As shown in FIG. 8 (a), in a state where the sheet body 2 is accommodated completely in the sheet accommodating body 3, the front wall 30c of the sheet accommodating body 3 and the front wall 40a of the handle 4 are in contact with each other. In this state, the pin body 42a of the switch mechanism 42 is pressed rearward with respect to the handle 4 (rightward in FIG. 8 (a)) by the front wall 30c of the sheet accommodating body 3. This causes the movable terminal 42d of the switch mechanism 42 to be separated from the fixed terminal 42c as indicated by the broken line in FIG. 6 and thereby the battery 41 goes off. That is, in the state shown in FIG. 8 (a), since the voltage of the battery 41 shown in FIG. 6 is not supplied to the boosting circuit 43 and the monitoring circuit 44, no ozone is generated from the sheet body 2 and the remaining battery power meter 44a and the power lamp 44b of the monitoring circuit 44 shown in FIG. 7 are in an off state.

From this state, when the handle 4 is gripped and the sheet body 2 is pulled out of the sheet accommodating body 3 as shown in FIG. 8 (b), the pressing force from the front wall 30c of the sheet accommodating body 3 on the pin body 42a is released and the pin body 42a moves forward with respect to the handle 4 (leftward in FIG. 8 (b)). This causes the movable terminal 42d of the switch mechanism 42 to come into contact with the fixed terminal 42c as indicated by the solid line in FIG. 6 and thereby the battery 41 goes on. That is, as shown in FIG. 8 (b), when the sheet body 2 is pulled out of the sheet accommodating body 3, the voltage of the battery 41 is supplied to the boosting circuit 43 and the monitoring circuit 44, a boosted alternate-current or pulsed voltage is supplied from the boosting circuit 43 to the electrodes 21, 22 of the sheet body 2, and the remaining battery power meter 44a and the power lamp 44b of the monitoring circuit 44 are turned on.

Figure 9:
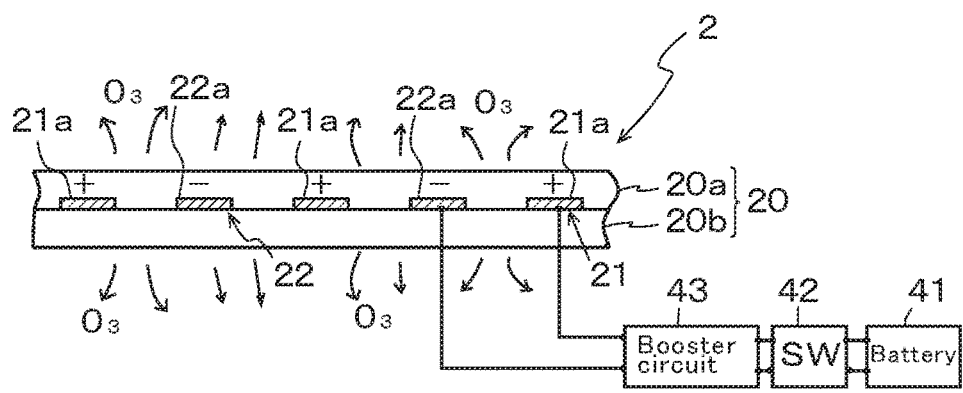
FIG. 9 is a schematic view showing a state where ozone is generated from the sheet body.

FIG. 9 is a schematic view showing a state where ozone is generated from the sheet body 2.

When the alternate-current or pulsed voltage is applied from the boosting circuit 43 to the electrodes 21, 22 of the sheet body 2 as shown in FIG. 9, the polarity of the comb teeth 21a of the electrode 21 and the polarity of the comb teeth 22a of the electrode 22 then become opposite and thereby discharging occurs between the comb teeth 21a and 22a, so that ozone $O_3$ is generated. As a result, a large amount of ozone $O_3$ is emitted above and below the sheet body 2 as indicated by the arrows and thereby bacteria therearound are removed.

Meanwhile, when the sheet body 2 is pulled out of the sheet accommodating body 3 as shown in FIG. 8 (b), the rotating body 31 rotates and the elastic force accumulating part 5A of the rewinding mechanism 5 functions such that the moving body 53 moves leftward on the rotating spiral rod 52 as shown in FIG. 5. As a result, the coil spring 55 is compressed so that an elastic force is accumulated.

When the sheet body 2 is pulled out by a desired length and then released, the compression force on the coil spring 55 and therefore the elastic force are released. That is, the coil spring 55 is restored in a stretching manner to press the moving body 53 of the elastic force accumulating part 5A rightward. This causes the moving body 53 to move rightward while rotating the spiral rod 52 reversely and attempt to thereby rotate the rotating body 31 reversely. However, upon this, the stopper part 5B of the rewinding mechanism 5 functions to inhibit the rotating body 31 from rotating reversely. As a result, the sheet body 2, even if it is released, stays pulled out not to be rewound.

The user can thus grip the handle 4 shown in FIG. 8 (b) to pull the sheet body 2 out of the sheet accommodating body 3 to a desired length and keep the length.

Figure 10:
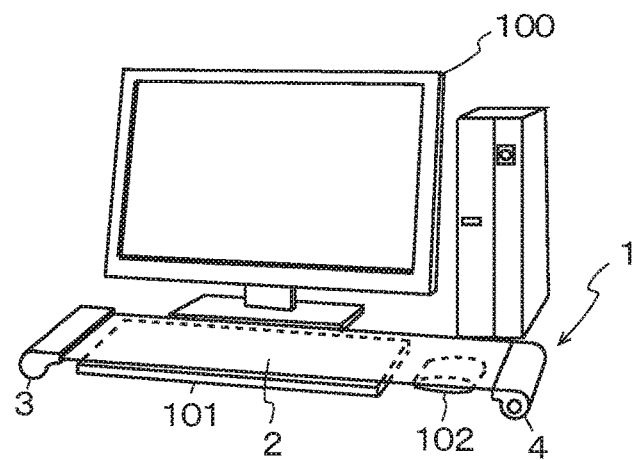

FIG. 10 is a perspective view showing an example in which the sterilizing sheet 1 is used to sterilize, for example, a desktop personal computer's keyboard and the like.

As mentioned above, the sterilizing sheet 1 is arranged such that the length of pull-out of the sheet body 2 can be adjusted. Hence, if sterilization of a desktop personal computer's keyboard and mouse is required, the sheet body 2 can be pulled out to a length at which the keyboard 101 and the mouse 102 of the desktop personal computer 100 can be covered, and then overlaid on the keyboard 101 and the mouse 102, as shown in FIG. 10. Upon this, the flexible sheet body 2 becomes deformed correspondingly to the shape of the keyboard 101 and the mouse 102. In this state, since the sheet accommodating body 3 and the handle 4 are separated, the battery 41 shown in FIG. 6 is in an on state, as mentioned above. As a result, ozone is emitted from the sheet body 2 to warp around not only the surface of the keyboard 101 but also the side surfaces of the key buttons and narrow gap portions at the back of the key buttons (not shown) to moreover sterilize the keyboard 101 thoroughly. During this sterilizing operation, it is possible to confirm the remaining battery power and/or the operating time by looking at the remaining battery power meter 44a and/or the power lamp 44b of the monitoring circuit 44 shown in FIG. 7.

After completion of the sterilizing operation, when the handle 4 is gripped to pull the sheet body 2 and rotate the rotating body 31 shown in FIG. 5 slightly in the direction of pull-out of the sheet body 2, the stopper part 5B functions such that the reverse rotation inhibited state of the rotating body 31 is released. As a result, the moving body 53 of the elastic force accumulating part 5A moves rightward while rotating the spiral rod 52 reversely and thereby rotates the rotating body 31 reversely. This causes the sheet body 2 to be rewound back around the rotating body 31 and accommodated within the sheet accommodating body 3.

In the state where the sheet body 2 is rewound, the sterilizing sheet 1 has a compact form in which the sheet accommodating body 3 and the handle 4 are aligned, as shown in FIG. 8 (a). Further, since the front wall 30c of the sheet accommodating body 3 and the front wall 40a of the handle 4 are in contact with each other, the pin body 42a of the switch mechanism 42 is pressed rearward by the front wall 30c of the sheet accommodating body 3, so that the battery 41 goes off as indicated by the broken line in FIG. 6.

Figure 11A:
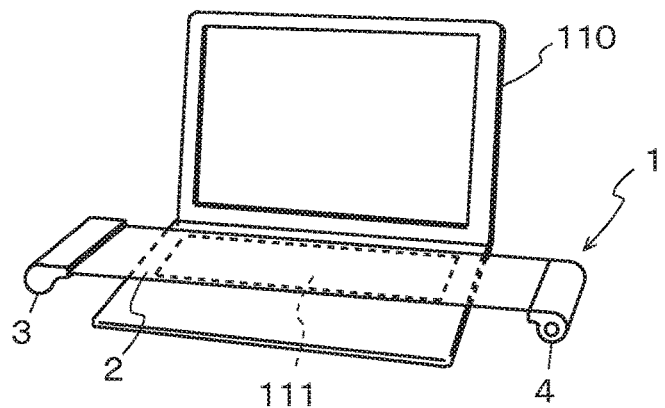
FIGS. 11(*a*) and 11(*b*) are perspective views showing examples in which the sterilizing sheets are used to sterilize other electronic devices, where FIG. 11 (*a*) shows an example of use for sterilization of a notebook personal computer and FIG. 11 (*b*) shows an example of use for sterilization of a smartphone.
Figure 11B:
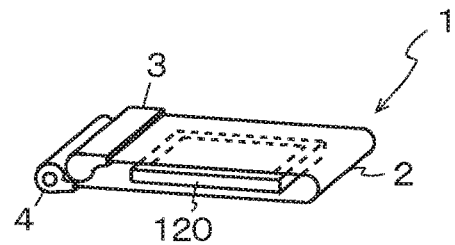
Figure 12A:
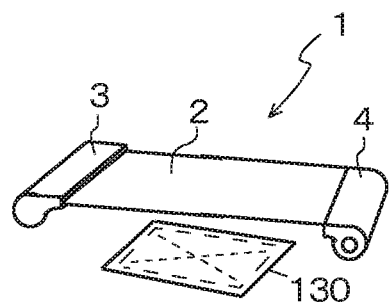
FIGS. 12(*a*), 12(*b*), 12(*c*), 12(*d*) and 12(*e*) are perspective views showing examples in which the sterilizing sheets are used for sterilization target objects other than electronic devices, where FIG. 12 (*a*) shows an example of use for sterilization of a dust cloth, FIG. 12 (*b*) shows an example of use for sterilization of a towel, FIG. 12 (*c*) shows an example of use for sterilization of a chopping board, FIG. 12 (*d*) shows an example of use for sterilization of a slipper, and FIG. 12 (*e*) shows an example of use for sterilization of a toy.
Figure 12B:
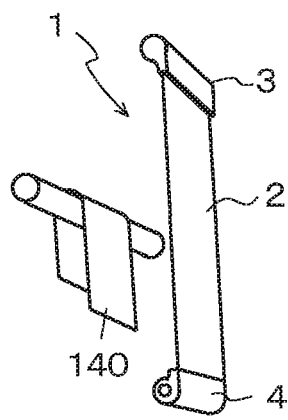
Figure 12C:
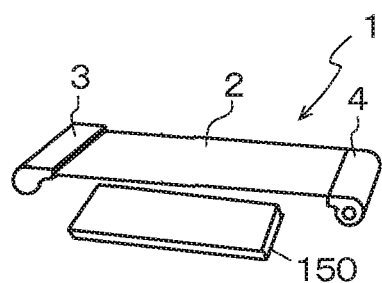
Figure 12D:
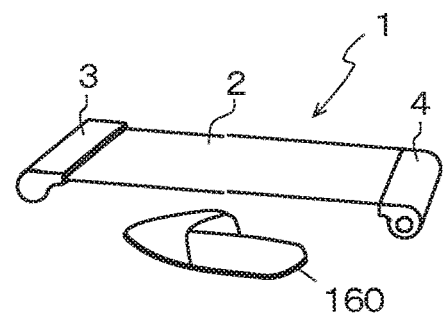
Figure 12E:
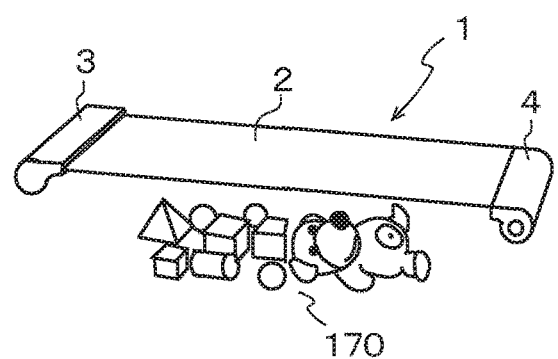

FIG. 11 is a perspective view showing an example in which the sterilizing sheet 1 is used to sterilize other electronic devices, where FIG. 11 (a) shows an example of use for sterilization of a notebook personal computer and FIG. 11 (b) shows an example of use for sterilization of a smartphone.

The sheet body 2 of the sterilizing sheet 1, which can be adjusted in length and is also flexible as mentioned above, can cover the keyboard part 111 of the notebook personal computer 110 as shown in FIG. 11 (a) or wrap the entire smartphone 120 to sterilize these devices.

Thus, in accordance with the sterilizing sheet 1 according to this embodiment, the sterilizing sheet 1 can by itself be used to sterilize not only a personal computer's keyboard but also electronic devices of various sizes such as a mouse and a smartphone.

The fact that the sterilizing sheet 1 according to this embodiment can also sterilize various types of sterilization target objects other than electronic devices will now be discussed briefly.

FIG. 12 is a perspective view showing an example in which the sterilizing sheet is used for sterilization target objects other than electronic devices, where FIG. 12 (a) shows an example of use for sterilization of a dust cloth, FIG. 12 (b) shows an example of use for sterilization of a towel, FIG. 12 (c) shows an example of use for sterilization of a chopping board, FIG. 12 (d) shows an example of use for sterilization of a slipper, and FIG. 12 (e) shows an example of use for sterilization of a toy.

As shown in FIG. 12 (a), when the sterilizing sheet 1 is overlaid and activated over a wiping cloth 130 such as a kitchen cloth or a dust cloth, not only can germs and/or food poisoning bacteria attached to the wiping cloth 130 be removed, but mold odor or the like can also be removed.

Thus using the sterilizing sheet 1 allows the wiping cloth 130 to be sterilized without using chemicals or water and therefore the burden on the environment to be reduced.

Since towels with which hands and faces are wiped are left hanging in moist places for a long period of time after use, germs are likely to develop. In such situation, as shown in FIG. 12 (b), the sterilizing sheet 1 is expanded to a length at which the towel 140 can be covered and hung on a wall with a magnet or a Velcro (registered trademark) and then activated. The towel 140 is thus sterilized and kept clean all day.

Also, food poisoning bacteria may be attached to chopping boards on which raw meat and raw fish are cut and may be left to develop thereon even after being washed with dishwashing detergent. Also in such a case, as shown in FIG. 12 (c), the sterilizing sheet 1 can be overlaid and activated on the chopping board 150 to remove remaining food poisoning bacteria. While the chopping board 150 is commonly sterilized under hot water, chlorine bleach, or the like, using the sterilizing sheet 1 can prevent a possible hot water burn or burden on the environment by bleach.

Further, a slipper 160, which is not machine-washable, is likely to be left uncleaned. However, as shown in FIG. 12 (d), the slipper 160 can be covered and sterilized with the sterilizing sheet 1 to be kept clean.

Small objects such as toys are difficult to clean. In particular, cleaning a number of small objects one by one takes a great deal of time and effort. In such a case, as shown in FIG. 12 (e), the sterilizing sheet 1 can be overlaid and activated entirely on a number of toys 170 to sterilize the toys 170 at one time.

Second Embodiment

Next will be described a second embodiment of the present invention.

Figure 13:
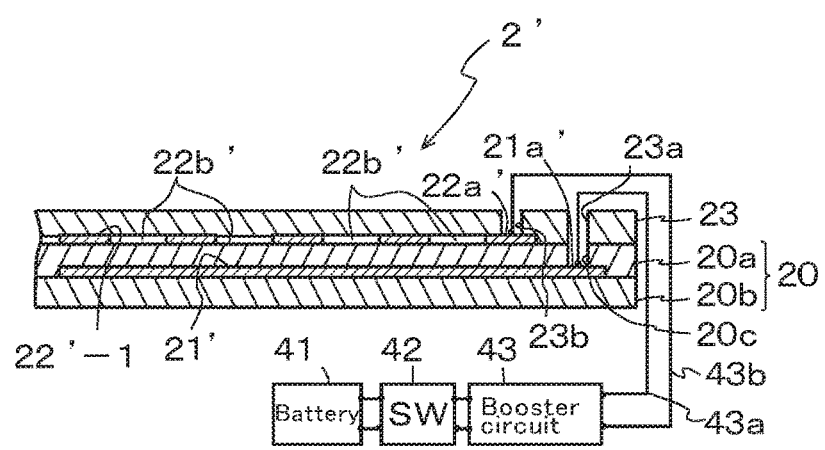
FIG. 13 is a cross-sectional view showing a substantial part of a sterilizing sheet according to a second embodiment of the present invention.
Figure 14:
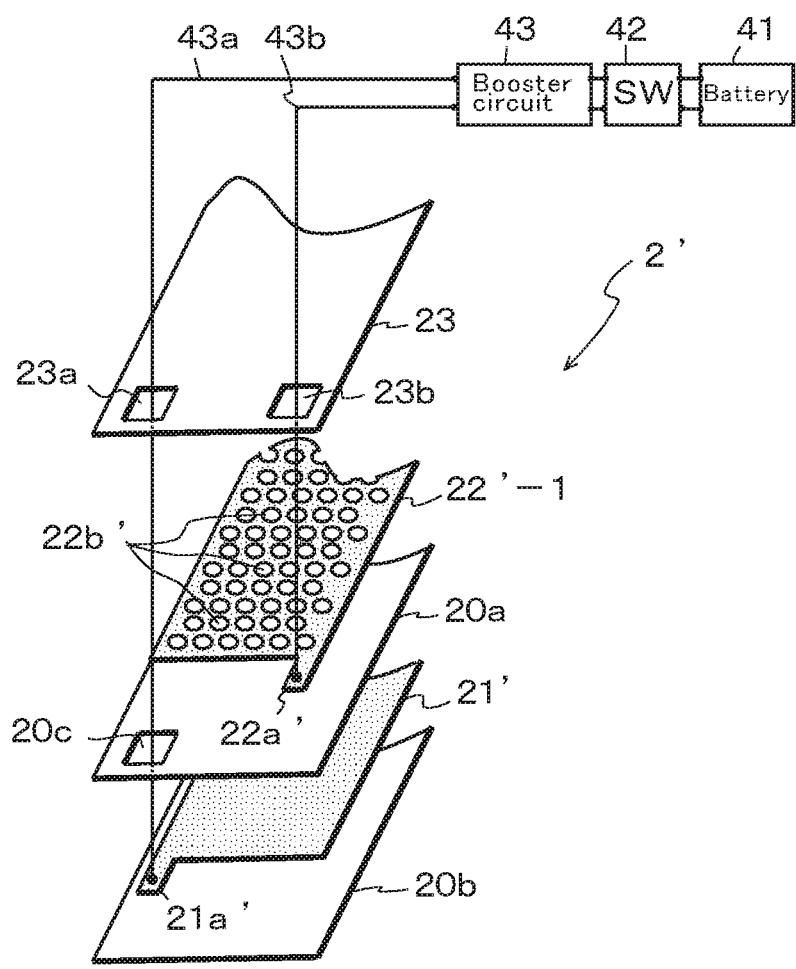
FIG. 14 is an exploded perspective view of the substantial part shown in FIG. 13.

FIG. 13 is a cross-sectional view showing a substantial part of a sterilizing sheet according to the second embodiment of the present invention, and FIG. 14 is an exploded perspective view of the substantial part shown in FIG. 13.

As shown in FIG. 13, the sterilizing sheet according to this embodiment includes a sheet body 2' having a structure different from that of the sheet body 2 according to the above-described first embodiment.

That is, only one electrode 21' is accommodated within the dielectric 20 and the other electrode 22'-1 is provided on the surface of the dielectric 20.

Specifically, as shown in FIG. 14, the solid electrode 21' is formed in a laminated manner on the lower dielectric layer 20b and the upper dielectric layer 20a is laminated on the dielectric layer 20b in a manner covering the electrode 21'. Moreover, the electrode 22'-1 having approximately the same shape as the electrode 21' is formed on the dielectric layer 20a. Further, a protective layer 23 is laminated on the electrode 22'-1.

A terminal part 21a' is provided at a corner of the electrode 21' and a rectangular feed port 20c through which the terminal part 21a' is exposed is formed at a corner of the upper dielectric layer 20a. Further, a feed port 23a in communication with the feed port 20c is provided at a corner of the protective layer 23. Moreover, a wire 43a extending from one of the output terminals of the boosting circuit 43 is connected to the terminal part 21a' of the electrode 21' through the feed ports 23a and 20c.

On the other hand, a terminal part 22a' is provided at a corner of the electrode 22'-1 and a rectangular feed port 23b through which the terminal part 22a' is exposed is formed at a corner of the upper protective layer 23. Moreover, a wire 43b extending from the other output terminal of the boosting circuit 43 is connected to the terminal part 22a' of the electrode 22'-1 through the feed port 23b.

Further, a number of circular holes 22b' are bored at a regular interval in the electrode 22'-1 that is provided on the surface of the dielectric 20.

Like the sheet body 2 according to the above-described first embodiment, the sheet body 2' according to this embodiment is also formed entirely of polymeric resin. That is, not only are the dielectric layers 20a, 20b and the protective layer 23 respectively formed of polyimide resin, but the electrodes 21', 22'-1 are also formed of conductive polymer, an example of polymeric resin.

It is noted that in this embodiment, the protective layer 23, which is provided on the electrode 22'-1 existing on the surface of the dielectric 20, is not an essential member and, in some cases, may not necessarily be provided.

Figure 15A:
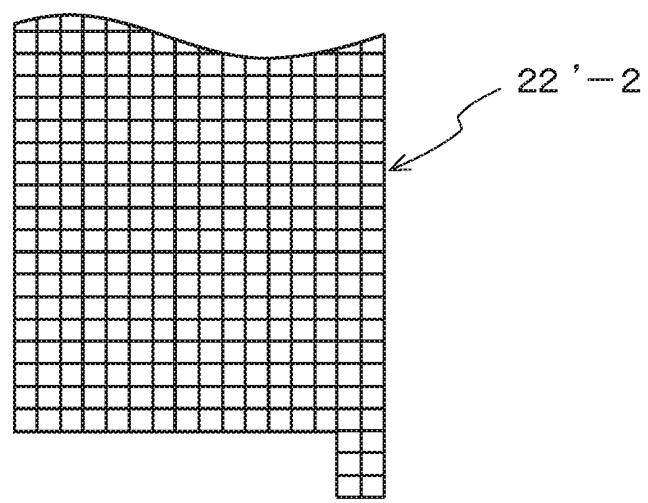
FIGS. 15(a) and 15(b) are plan views showing variations of electrodes according to the second embodiments.
Figure 15B:
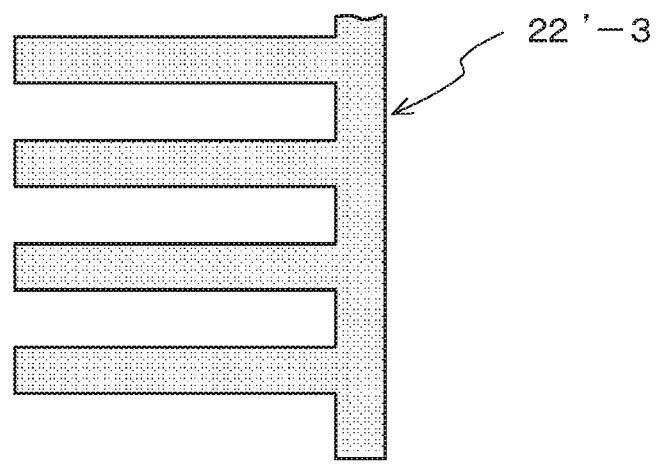

While in this embodiment, the electrode 22'-1 having a number of circular holes 22b' is applied as the other electrode, a meshed electrode 22'-2 may be applied as the other electrode as shown in FIG. 15 (a) or a comb-like electrode 22'-3 may be applied as the other electrode as shown in FIG. 15 (b).

Since the other configurations, operations, and effects are the same as those in the above-described first embodiment, the description thereof will be omitted.

It is noted that the present invention is not intended to be limited to the above-described embodiments, but may be variously varied and changed within the spirit and scope of the invention.

For example, while in the above-described embodiments, the electrodes 21, 22, 21', 22'-1 of the sheet bodies 2, 2' are also formed of conductive polymer, an example of polymeric resin like the dielectric 20, the electrodes 21, 22, 21', 22'-1 may be formed of metal foil such as copper or conductive ink such as carbon or silver.

Also, while the sheet body 2 according to the above-described first embodiment employs the structure in which the pair of comb-like electrodes 21, 22 are accommodated together within the dielectric 20 and the sheet body 2' according to the above-described second embodiment employs the structure in which the one electrode 21' is accommodated within the dielectric 20 and the other electrode 22'-1 is provided on the surface of the dielectric 20, the structure of the sheet body is not limited thereto. For example, a pair of electrodes may be formed in a flat-plate manner and the two electrodes may be arranged side by side at a regular interval or single electrodes may be formed together in a spiral shape and the pair of spiral electrodes may be fitted to each other at a regular interval.

Also, while the above-described embodiments illustrate the sterilizing sheet 1 including the rewinding mechanism 5, the switch mechanism 42, and the monitoring circuit 44, it will be appreciated that a sterilizing sheet not including some or all of these components also falls within the scope of the invention.

Further, the battery 41 and the boosting circuit 43, which are provided in the handle 4 in the above-described embodiments, may be provided in the sheet accommodating body 3.

Furthermore, while in the above-described embodiments, the battery 41 is used as a power source for high portability, the alternate-current commercial power source may be used instead of the battery 41 or a USB cable connected to an external power source may be connected electrically to the switch mechanism 42 in the handle 4.

REFERENCE SIGNS LIST

1 . . . sterilizing sheet, 2, 2' . . . sheet body, 3 . . . sheet accommodating body, 4 . . . handle, 5 . . . rewinding mechanism, 5A . . . elastic force accumulating part, 5B . . . stopper part, 20 . . . dielectric, 20a, 20b . . . dielectric layer, 20c, 23a, 23b . . . feed port, 21, 22, 21', 22'-1 to 22'-3 . . . electrode, 21a, 22a . . . comb teeth, 22b' . . . circular hole, 21a', 22a' . . . terminal part, 23 . . . protective layer, 30, 40 . . . case, 30a . . . right wall, 30b . . . left wall, 30c, 40a . . . front wall, 31 . . . rotating body, 31a . . . right-hand shaft, 31b, 31c . . . bearing, 40b . . . hole, 40c . . . upper wall, 41 . . . battery, 42 . . . switch mechanism, 42a . . . pin body, 42b . . . spring, 42c . . . fixed terminal, 42d . . . movable terminal, 43 . . . boosting circuit, 43a, 43b . . . wire, 44 . . . monitoring circuit, 44a . . . remaining battery power meter, 44b . . . power lamp, 50 . . . cylindrical body, 51 . . . planetary gear train, 52 . . . spiral rod, 53 . . . moving body, 53a, 54 . . . rectangular cylindrical body, 55 . . . coil spring, 100 . . . desktop personal computer, 101 . . . keyboard, 102 . . . mouse, 110 . . . notebook personal computer, 111 . . . keyboard part, 120 . . . smartphone, 130 . . . wiping cloth, 140 . . . towel, 150 . . . chopping board, 160 . . . slipper, 170 . . . toy, $O_3$ . . . ozone

The invention claimed is:

1. A sterilizing sheet device comprising:
a flexible sheet body formed by a sheet-like dielectric and a pair of electrodes, at least one of the pair of electrodes being accommodated within the sheet-like dielectric;
a sheet accommodating body in which the flexible sheet body is accommodated in a manner capable of being pulled out and rewound;
a handle attached to the leading end of the flexible sheet body;
a power source; and
a boosting circuit accommodated in the sheet accommodating body or the handle and boosting a voltage from the power source to a necessary voltage to generate ozone by the pair of electrodes.

2. The sterilizing sheet device according to claim 1, wherein
at least the sheet-like dielectric of the flexible sheet body is formed of polymeric resin.

3. The sterilizing sheet device according to claim 1, wherein each of
the pair of electrodes is formed in a comb shape and comb teeth of the pair of electrodes are engaged with each other at a regular interval.

4. The sterilizing sheet device according to claim 1, further comprising
   a rewinding mechanism provided to automatically rewind the flexible sheet body, when pulled out of the sheet accommodating body, back into the sheet accommodating body.

5. The sterilizing sheet device according to claim 1, wherein
   the power source is a battery accommodated in the sheet accommodating body or the handle.

6. The sterilizing sheet device according to claim 1, further comprising:
   a switch mechanism provided to turn on the power source when the flexible sheet body is pulled out of the sheet accommodating body and to turn off the power source when the flexile sheet body is accommodated in the sheet accommodating body.

7. The sterilizing sheet device according to claim 1, further comprising:
   a monitoring circuit for displaying some or all of an on or off state of the power source, a remaining battery power, and an operating time, provided on the sheet accommodating body or the handle.

8. The sterilizing sheet device according to claim 1, wherein
   one electrode of the pair of electrodes is accommodated within the sheet-like dielectric and the other electrode with a number of holes or in a comb shape is disposed on the surface of the sheet-like dielectric in a manner opposed to the one electrode.

\* \* \* \* \*